(12) United States Patent
Goldstein et al.

(10) Patent No.: US 7,449,203 B2
(45) Date of Patent: Nov. 11, 2008

(54) **COSMETIC COMPOSITIONS AND METHODS COMPRISING *RHODIOLA ROSEA***

(75) Inventors: Mindy S. Goldstein, Plainview, NY (US); Chia Wen Chen, Bronxville, NY (US); Thomas Mammone, Farmingdale, NY (US); David C. Gan, South Lake, TX (US)

(73) Assignee: E-L Management Corporation, New York, NY (US)

( * ) Notice: Subject to any disclaimer, the term of this patent is extended or adjusted under 35 U.S.C. 154(b) by 160 days.

(21) Appl. No.: 11/167,390

(22) Filed: Jun. 27, 2005

(65) Prior Publication Data

US 2006/0002871 A1   Jan. 5, 2006

Related U.S. Application Data

(60) Provisional application No. 60/584,214, filed on Jun. 30, 2004.

(51) Int. Cl.
*A61K 36/00* (2006.01)
*A61K 7/06* (2006.01)

(52) U.S. Cl. ............................. 424/725; 424/74; 424/59

(58) Field of Classification Search .................. 424/773
See application file for complete search history.

(56) References Cited

U.S. PATENT DOCUMENTS

| | | | |
|---|---|---|---|
| 5,641,480 A | 6/1997 | Vermeer | |
| 5,653,970 A | 8/1997 | Vermeer | |
| 6,110,451 A | 8/2000 | Matz et al. | |
| 6,132,724 A | 10/2000 | Blum | |
| 6,211,246 B1 * | 4/2001 | Gelotte et al. | 514/653 |
| 6,323,189 B1 | 11/2001 | Hardinge-Lyme | |
| 6,365,630 B1 | 4/2002 | Fisher et al. | |
| 6,399,116 B1 | 6/2002 | Xiu | |
| 6,541,480 B2 | 4/2003 | Shimamoto et al. | |
| 6,551,627 B1 | 4/2003 | Yoon et al. | |
| 6,566,313 B1 | 5/2003 | Hohenstein et al. | |
| 7,115,285 B2 * | 10/2006 | McKee et al. | 424/725 |
| 7,122,530 B2 * | 10/2006 | Bishop et al. | 514/168 |
| 2002/0127285 A1 | 9/2002 | Xiu | |
| 2005/0101632 A1 * | 5/2005 | Gagnon et al. | 514/313 |

FOREIGN PATENT DOCUMENTS

| | | |
|---|---|---|
| CN | 1078385 | 11/1993 |
| CN | 1078385 A | 11/1993 |
| CN | 1091279 | 8/1994 |
| CN | 1091279 A | 8/1994 |
| CN | 1095919 | 12/1994 |
| CN | 1306816 | 8/2001 |
| CN | 1310021 | 8/2001 |
| JP | 11335236 | 12/1999 |
| JP | 2001048768 A | 2/2001 |
| JP | 2001316239 A | 11/2001 |
| KR | 2003012562 A | 3/2001 |
| KR | 2001016591 A | 2/2003 |
| RU | 2137488 | 9/1999 |
| RU | 2211692 | 9/2003 |

OTHER PUBLICATIONS

Rosavin, Rhodiola rosea, by Ameriden, http://risingstarlc.com/rosavin.htm.
Rhodiola rosea. Anti-Aging-Guide—Your plan to stay young; http://www.anti-aging-guide.com/RhodiolaRosea.html (Oct. 2003).
Derrida, The photochemistry of Rhodiola rosea root; http://www.anti-aging-guide.com/RhodiolaRosea.html (May 2003).
Kelly MD, Gregory S.; Rhodiola rosea research study; A Possible Plant Adaption http://www.smart-nutrition.net/Rhodiola-rosea.htm.
Dubichev et al., Study of Chemical Composition of Rhodiola Rosea Rhizomes Using HPLC Method, UDC 615.32-547.9:543.544 (published May 11, 1990).
Product Package/Label for Nefeli Intensive Wrinkle Care Day Cream (date unknown; coming into Applicants' possession no earlier than Jun. 2005).
Product Package/Label for Nefeli Intensive Day-Time Skin Brightening Cream (date unknown; coming into Applicants' possession no earlier than Jun. 2005).
Product Package/Label for Nefeli Intensive Wrinkle Care Night Cream (date unknown; coming into Applicants' possession no earlier than Jun. 2005).
Product Package/Label for Nefeli Eye Rejuvenating Mask (date unknown; coming into Applicants' possession no earlier than Jun. 2005).
Product Package Label for Nefeli Facial Rejuvenating Mask (date unknown; coming into Applicants' possession no earlier than Jun. 2005).
Collistar Linea Uomo Abdominals Treatment, Global New Products Database (Mar. 2003).
Collistar Abdomen & Hip Treatment, Global New Products Database (Apr. 2001).
Aveda Tourmaline Charged Hydrating Cream, Global New Products Database (Dec. 2003).

* cited by examiner

*Primary Examiner*—Christopher R Tate
*Assistant Examiner*—Randall Winston
(74) *Attorney, Agent, or Firm*—Yongzhi Yang; Julie H. Blackburn

(57) ABSTRACT

A cosmetic composition comprising a UV-protective amount of at least one rosavin, preferably present in an extract of *Rhodiola rosea* in a cosmetically acceptable vehicle, and methods of use thereof, including preventing or reducing the signs of photoaging.

5 Claims, 2 Drawing Sheets

COSMETIC COMPOSITIONS AND METHODS COMPRISING *RHODIOLA ROSEA*

The following invention claims priority under 35 USC 119e of U.S. provisional application 60/584,214 filed Jun. 30, 2004.

FIELD OF THE INVENTION

The present invention relates to skin care cosmetic compositions and methods. In particular, the present invention relates to novel cosmetic compositions and methods comprising *Rhodiola rosea* extracts.

BACKGROUND OF THE INVENTION

Numerous attempts have been made to reduce the detrimental effects of UV radiation on the skin. In fact, UV exposure to skin is believed to cause photoaging, a term used to describe the changes in appearance and/or function of human skin as a result of repeated exposure to sunlight. Of particular concern are wrinkles, coarseness, mottled pigmentation, sallowness, and related changes in the appearance of skin as a result of UV exposure.

Sunscreens are commonly used to prevent photoaging of skin areas that are exposed to sunlight. Sunscreens are topical preparations that contain ingredients that absorb, reflect and/or scatter UV light. Some sunscreens are based on opaque particulate materials including zinc oxide, titanium oxide, clays, and ferric chloride. However, because such preparations are visible and occlusive, many people consider those opaque formulations to be cosmetically unacceptable. Other sunscreens contain chemicals such as p-aminobenzoic acid (PABA), oxybenzone, dioxybenzone, ethylhexyl-methoxy cinnamate, octocrylene, octyl methoxycinnamate, and butyl-methoxydibenzoylmethane that are transparent or translucent on the skin. While these types of sunscreens may be more acceptable cosmetically, they are still relatively short-lived and susceptible to being removed by washing or perspiration. Moreover, there is a continuing trend in the art to provide naturally-derived skin care ingredients for application to the skin.

Therefore, there still remains a need for a novel composition and method for protecting the skin from UV-induced damage.

SUMMARY OF THE INVENTION

Figure 1:
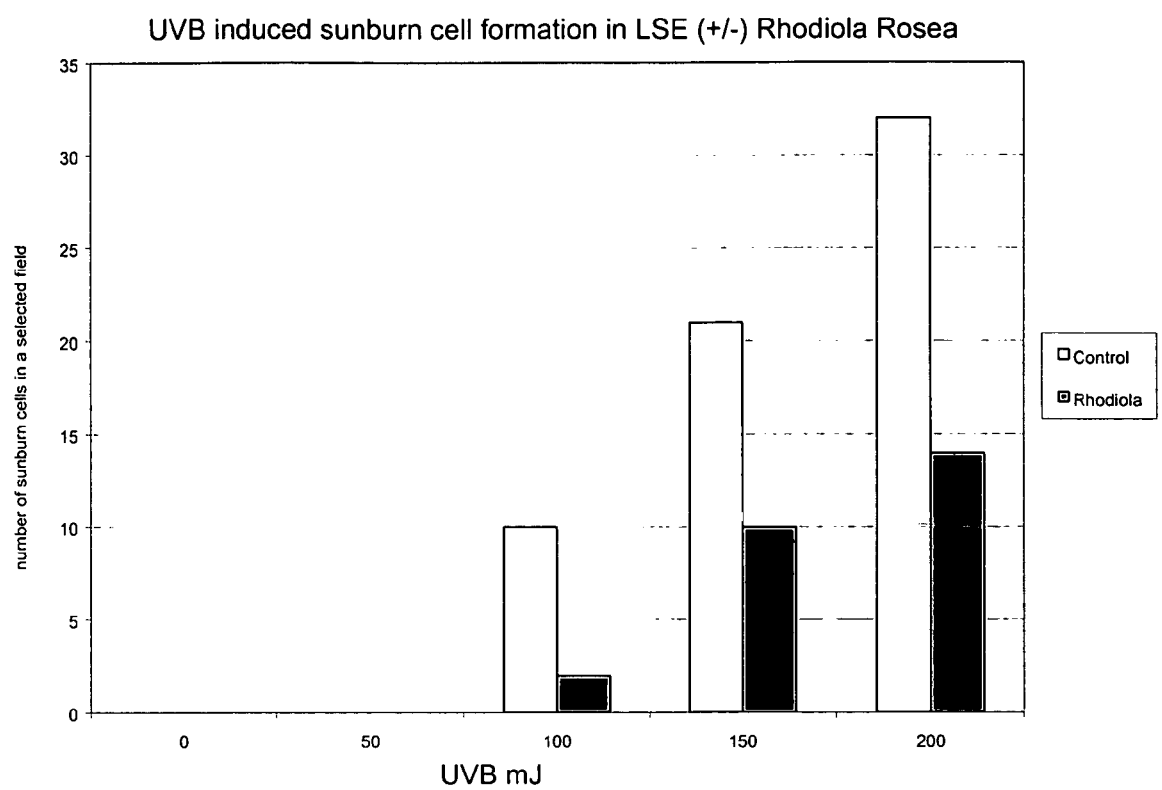
FIG. 1 provides a graphical depiction of the effect of *Rhodiola rosea* on sunburn cells.

The present invention comprises a cosmetic composition comprising a UV-protective amount of at least one rosavin. In a preferred embodiment, the rosavin is present in a plant extract. In one embodiment, the extract is an extract of *Rhodiola rosea* in a cosmetically acceptable vehicle.

The present invention further comprises a method of preventing or reducing the signs of photoaging comprising applying a composition comprising a UV-protective amount of at least one rosavin. In one embodiment, the rosavin is contained in an extract of *Rhodiola rosea* and a cosmetically acceptable vehicle.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified. By "effective amount" is meant an amount sufficient to cause a reduction in the effects of UV-damage.

The present invention is predicated on the observation that certain *Rhodiola rosea* extracts have the surprising ability to protect skin cells against the damaging effects of UV radiation. In further studies, it was eventually found that specific phenylpropanoids, in the extracts, collectively known as rosavins, are a principle protective component of the extract. Rosavins are components specific to *Rhodiola rosea*. While components of *Rhodiola rosea* have been identified as having various types of biological activity (Gregory S. Kelly, N D, "*Rhodiola rosea*: A Possible Plant Adaptogen," Alternative Medicine Review, Thorne Research, Inc., 2001), it was unexpected that the rosavins are primarily responsible for the UV-protective properties of *Rhodiola rosea* extracts.

As a background, the genus *Rhodiola* comprises several species of plants in the Crassulacea family and is generally found in the arctic mountain regions of Siberia. The root of the plant is used medicinally and is also known as "Arctic root" or "Golden root" and more recently as "Crenulin." *Rhodiola* has been used for hundreds of years to treat cold and flu-like symptoms, promote longevity and increase the body's resistance to physical and mental stresses. There are approximately 200 species of the genus *Rhodiola*, and the phytochemistry and pharmacological properties of these plants may depend upon which species is being used (Komarov, 1939; Saratikov 1974; Kurkin and Zapesochnaya 1986).

The species *Rhodiola rosea* grows primarily in dry, sandy ground at high altitudes in the arctic areas of Europe and Asia. For centuries, *Rhodiola rosea* has been used in the traditional medicine of Russia, Scandinavia, and other countries. Recently, *Rhodiola rosea* has gained popularity as an oral supplement as an adaptogen. Adaptogens are reported to significantly accelerate the recovery process after illness, increase availability of energy, aid in reducing stress, increase endurance and generate greater mental alertness.

The chemical composition of *Rhodiola Rosea* is well documented. Principal constituents in *R. rosea* are cinnamyl alcohol vicyanoside rosavin, rosin, rosarin, (collectively the rosavins) and hydroxyphenylethanol-2-D-glucopyranoside (salidroside, also known as rhodioloside) (Saratikov et al. 1968; Kurkin and Zapesochnaya 1986 a,b). The presence of rosavins in *Rhodiola* seems to be specific to *R. rosea* only (Kurkin and Zapesochnaya, 1996 a,b; Dubichev et al. 1991), while the presence of salidroside was shown in all plant species of the genus *Rhodiola* (Barnaulov et al. 1965; Wang et al. 1992 a,b; Kang et al. 1992; Yoshikawa et al. 1996; Linh et al. 2000). For example, *R. crenulata* is a medicinal plant in Uzbekistan, China and other Asian countries with the salidroside believed to be the active ingredient (Wang et al. 1992 b; Cui S et al. 2003). See also U.S. Publication No. 20020127285 (uses *Rhodiola crenulata*, for its salidroside content at 0.5-10%).

Products incorporating *Rhodiola rosea* exist in the market, claiming a dramatic effect on people due to its origin and the proprietary process in which it is manufactured. This is very important because the correct proportions of phytonutrients such as rosavin, rosin, rosarin and salidroside, unless controlled, alter with the season and when consumed can change the entire response to the body. As an example, the product, Rosavin™ (Siberian *Rhodiola rosea*), processed by Dr. Zakir Ramanzanov's proprietary process is marketed for oral intake for various medicinal benefits. Some claiming to be *Rhodiola rosea* contain very little rosavin and high amounts of heavy metals and still others do not contain rosavin, rosarin or rosin at all.

*Rhodiola* extracts or concentrates of the effective ingredients of *Rhodiola*, are obtained by contacting the plant part with a suitable solvent, such as water, alcohol, methanol, or any other solvents, or mixed solvents. The choice of the solvent may be made routinely, e.g., based on the properties of the active ingredient that is to be extracted or concentrated by the solvent. Preferred active ingredients of *Rhodiola rosea* include but are not limited to, rosavins, salidroside and tyrosol. These ingredients can be extracted in the same step, e.g., using an alcoholic or water solvent, or they may be extracted individually, each time using a solvent which is especially effective for extracting the particular target ingredient from the plant.

In initial experiments, it has been surprisingly discovered in the present invention that an extract of *Rhodiola rosea* effectively protects the skin from photodamage. Specifically, while not wishing to be bound by any theory, it is believed that specific extracts of *Rhodiola rosea* increase DNA repair and therefore protect against UV-induced skin damage.

*Rhodiola rosea* is believed to have six distinct groups of chemical compounds: phenylpropanoids including rosavins, rosin and rosarin; phenylethanol derivatives including salidroside (rhodioloside) and tyrosol; flavonoids including rodiolin, rodionin, rodiosin, acetylrodalgin and tricin; monoterpenes including rosiridol and rosaridin; triterpenes including daucosterol and beta-sitosterol; and phenolic acids including chlorogenic and hydroxycinnamic and gallic acids. See "*Rhodiola Rosea* A Phytomedical Overview," Herbal-Gram, Richard P. Brown et al., 2002.

As subsequent experiments show (see Example 2) the rosavins are a primary active component in *Rhodiola* extracts. Rosavins are relatively easily isolated from plant material containing them by known chemical techniques. Effective amounts of isolated rosavins, i.e., any one or a combination of rosavins, can therefore be used in a topical composition to achieve the UV-protective effect. The effective amount of isolated rosavin incorporated into a composition will ordinarily be in the range of from 0.0001% to 0.1%, preferably from 0.001% to 0.008% and most preferably 0.004% by weight of the total composition. However, as a practical matter, it is also possible, and perhaps more convenient, to include a rosavin-containing compound in the composition to achieve a protective rosavin effect. In a preferred embodiment, an extract of any plant containing rosavins is appropriate for use in the compositions or methods of the invention. However, *Rhodiola rosea* extracts containing rosavins are available from a wide range of commercial sources (Amax NutraSource Inc., Eugene, Oreg.; Solgar Vitamin and Herb, Leonia, N.J.; Jarrow Formulas, Inc., Los Angeles, Calif.), and thus most convenient.

Concentrations of the active rosavins may vary from extract to extract, so as a guideline, it is recommended to use the amount of extract that would provide an equivalent concentration of isolated rosavin as noted above. In addition, as shown in the examples below, although rosavins are the principle active component in achieving UV-protection, additional components, although not necessarily very effective on their own, may be present in the plant extracts that can have some contributory activity. In one preferred embodiment, the extract of *Rhodiola rosea* contains a combination of rosavins and salidrosides. The rosavins are present in an amount of from 1% to 50%, preferably from 2% to 40%, and most preferably from 4% to 5% of the extract. The salidrosides are present in an amount from 0.1% to 50%, preferably from 0.5% to 40%, and most preferably from 1% to 5% of the composition and from 0.0001% to 30%, preferably from 0.001% to 20% and most preferably from 0.01% to 10% of the extract. The preferred *Rhodiola rosea* extract is commercially available from Amax Nutrasource Inc. in Eugene, Oreg.

The amount of extract will vary depending on the formulation and the performance desired, and also on the concentration of the rosavins in the extract, as noted above. A typical *Rhodiola rosea* extract, e.g., one containing from 0.0001% to 0.1% of rosavins, is used in an amount from 0.0001% to 90% by weight of the composition is used. Preferably, *Rhodiola rosea* is used in an amount from 0.001% to 70%, and most preferably, from 0.1% to 10%.

In an alternate embodiment, the present invention includes a sunscreen. Suitable sunscreens include water soluble sunscreens (such as Eusolex 232); oil soluble sunscreens (such as octyl methoxycinnamate); inorganic sunscreens (such as titanium dioxide, zinc oxide) and organic sunscreens (such as camphor derivatives, cinnamates, salicylates, benzophenones, triazines, PABA derivatives, diphenylacrylate derivatives, and dibenzoylmethane derivatives.)

The amount will vary depending on the formulation and the performance desired. The sunscreen is used in an amount from 0.1% to 50% by weight of the composition. Preferably, the sunscreen is used in an amount from 1% to 40% and most preferably, an amount of from 5% to 30%.

The composition further comprises a cosmetically acceptable vehicle that is suitable for topical application to skin, hair and/or nails. Cosmetically acceptable vehicles are well known in the art and are selected based on the end use of the application. For example, vehicles of the present invention include, but are not limited to, those suitable for application to the skin. Such vehicles are well known to those of ordinary skill in the art, and can include one or more compatible liquid or solid filler diluents or vehicles which are suitable for application to the skin. The exact amount of vehicle will depend upon the level of any other optional ingredients that one of ordinary skill in the art would classify as distinct from the vehicle (e.g., other active components). The compositions of the present invention preferably comprise from about 75% to about 99.99%, more preferably from about 85% to about 99.99%, and most preferably from about 93% to about 98%, by weight of the composition, of a vehicle.

The vehicle and the compositions herein can be formulated in a number of ways, including but not limited to emulsions. For example, suitable emulsions include oil-in-water, water-in-oil, water-in-oil-in-water, oil-in-water-in-oil, and oil-in-water-in-silicone emulsions. Preferred compositions comprise an oil-in-water emulsion.

The compositions of the present invention can be formulated into a wide variety of product types, including shampoos, creams, waxes, pastes, lotions, milks, mousses, gels, oils, tonics and sprays. Preferred compositions are formulated into lotions, creams, gels, shampoos and sprays. These product forms may be used for a number of applications, including but not limited to, hand and body lotions, cold creams, facial moisturizers, anti-acne preparations, topical analgesics, make-ups/cosmetics including foundations, eyeshadows, lipsticks and the like. Any additional components required to formulate such products vary with product type and can be routinely chosen by one skilled in the art.

If compositions of the present invention are formulated as an aerosol and applied to the skin as a spray-on product, a propellant may be added to the composition. Examples of suitable propellants include chlorofluorinated lower molecular weight hydrocarbons. A more complete disclosure of propellants useful herein can be found in Sagarin, *Cosmetics Science and Technology*, 2$^{nd}$ Edition, Vol. 2, pp. 443-465 (1972).

Other Components

The formulation also can comprise other components that may be chosen depending on the carrier and/or the intended use of the formulation. Additional components include, but are not limited to antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/Eicosene copolymer); water soluble film-formers (such as hydroxypropyl methylcellulose); oil-soluble film formers (such as hydrogenated C-9 Resin); moisturizing agents, such as cholesterol; cationic polymers (such as Polyquatenium 10); anionic polymers (such as xanthan gum); vitamins (such as tocopherol); and the like.

The compositions can also encompass one or more additional active components, and as such can be either cosmetic or pharmaceutical compositions. Examples of useful actives include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, depigmenting agents, wound-healing agents, vitamins, corticosteroids, tanning agents or hormones. More specific examples of useful active agents include retinoids such as retinol, and esters, acids, and aldehydes thereof; ascorbic acid, and esters and metal salts thereof, tocopherol and esters and amide derivatives thereof; shark cartilage; milk proteins; alpha- or beta-hydroxy acids; DHEA and derivatives thereof; topical cardiovascular agents; clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, hydrocortisone, hydrocortisone 21-acetate, hydrocortisone 17-valerate, hydrocortisone 17-butyrate, betamethasone valerate, betamethasone diprionate, triaminolone acetonide, fluocinonide, clobetasol, proprionate, benzoyl peroxide, crotamiton, propranol, promethazine, and mixtures thereof.

Particularly preferred embodiments of the present formulations are skin care lotions or creams used as an anti-aging product. To that end, the present formulations are combined with agents that are moisturizers, emollients or humectants. Examples of useful combinations are oils, fats, waxes, esters, fatty acid alcohols, fatty acid ethoxylates, glycols, sugars, hyaluronic acid and hyaluronates, dimethicone, cyclomethicone, and the like. Further examples can be found in the International Cosmetic Ingredient Dictionary, CTFA, Sixth Edition, 1995.

Method of Reducing the Signs of Photoaging

The present inventive compositions are particularly useful as products as methods of retarding the signs of photoaging and protecting the skin from UV damage. As used herein, "photoaging" can include signs of aging such as skin atrophy and means the thinning and/or general degradation of the dermis caused by free radical damage which is often characterized by an alteration and degeneration of collagen and/or elastin due to extrinsic factors such as photodamage caused by exposure to UV radiation. As used herein, "retarding the signs of photoaging" includes arresting, treating, or reversing the process of skin aging in mammalian skin. Examples of retarding skin aging include but is not limited to reduction of the appearance of lines and wrinkles, reduction of the effect of skin atrophy and reduction of the appearance of thinning.

Such methods comprise administering or topically applying to the skin a safe and effective amount of the composition of the present invention. The amounts of the components in the compositions will vary widely depending upon the level of regulation desired.

A preferred method of cosmetically or pharmaceutically treating the skin is via chronic topical application of a safe and effective amount of the novel composition to protect the skin. The amount of the composition and the frequency of topical application to the skin can vary widely, depending upon the individual's desired amount of protection for total coverage or on an as-needed basis. It is well within the purview of the skilled artisan, such as a dermatologist or other health care provider, to regulate pharmaceutical dosages according to patient needs. The method of the present invention is suitable for daily use.

It is suggested as an example that topical application range from about once per week to about 2 or 3 times daily, preferably from about 5 times a week to about 3 times daily, most preferably about once or twice per day. The compositions will comprise from 0.0001% to 0.5%, preferably from 0.001% to 0.01% and most preferably 0.002% 0.009% of the active components.

The following examples further illustrate the invention, but the invention is not limited thereto.

EXAMPLE 1

The following are two compositions within the scope of the present invention.

| TRADE NAME | CTFA NAME | PERCENT |
|---|---|---|
| Composition A | | |
| Lipocol C/Cetyl Alcohol NF | Cetyl Alcohol | 1.65 |
| Glyceryl Monostearate Pure | Glyceryl Stearate | 1.65 |
| Arlacel 165 | Glyceryl Stearate/PEG-100 Stearate | 6.60 |
| Lanette O | Cetearyl Alcohol | 1.10 |
| Softisan 378 | Caprylic/Capric/Myrstic/ Stearic Triglyceride | 0.50 |
| Silicone 200 (100 CTS.) | Dimethicone | 0.40 |
| Cetiol LC | Coco-Caprylate/Caprate | 3.60 |
| Tween 40 | Polysorbate 40 | 0.66 |
| Span 40 | Sorbitan Palmitate | 0.44 |
| Wickenol 161 | Dioctyl Adipate/Octyl Stearate/ Octyl Palmitate | 3.30 |
| Deionized Water | Purified Water | 74.0 |
| 1,3 Butylene Glycol | Butylene Glycol | 6.00 |
| Rhodiola Rosea 4% | Rhodiola Rosea Root Extract | 0.10 |
| Composition B | | |
| Satin Finish III-9 | Water/Phenyl Trimethicone/ Cyclomethicone/Dimethiconol/ Phosphoglycerides/Carbomer/ Triethanolamine | 50.0 |

-continued

| TRADE NAME | CTFA NAME | PERCENT |
| --- | --- | --- |
| Tristrat SDHA | Sodium Dehydroacetate | 0.10 |
| Disodium EDTA/ Trilon BD | Disodium EDTA | 0.14 |
| Glycerine USP 99% (Vegetable) | Glycerin | 3.00 |
| Dry Flo Pure 28-1850/Dry Flow Plus | Aluminum Starch Octenylsuccinate | 1.00 |
| Deionized Water | Purified Water | 41.71 |
| Carbopol 1382 | Acrylates/C10-30 Alkyl Acrylate Crosspolymer | 0.30 |
| Carbopol 980 | Carbomer | 0.35 |
| Glycerine USP 99% (Vegetable) | Glycerin | 1.00 |
| Keltrol T | Xanthan Gum | 0.20 |
| Deionized Water | Purified Water | 2.00 |
| Triethanolamine 99% | Triethanolamine | 0.10 |
| Rhodiola Rosea 4% | Rhodiola Rosea Root Extract | 0.10 |

EXAMPLE 1

The effect of *Rhodiola rosea* on UVB-induced sunburn cell formation in living skin equivalents (LSEs) is tested. Excised portions (8 mm) are taken from living skin equivalents (Organogenesis) and cultured over transwell membrane plates. These excised portions are pre-treated with *Rhodiola rosea* at 0.1 mg/ml (PBS) for 4 hours. After the post-incubation, these excised portions are UVB-irradiated at 0, 50, 100, 150 and 200 mJ/cm$^2$. Following a 24 hour post-incubation, these skin equivalents are fixed in formalin and stored at −4° C. These samples are then stained using H&E staining. Sections are then evaluated using a microscope at 400× magnification. A section is selected from each sample and counts of sunburn cells were made.

Figure 2:
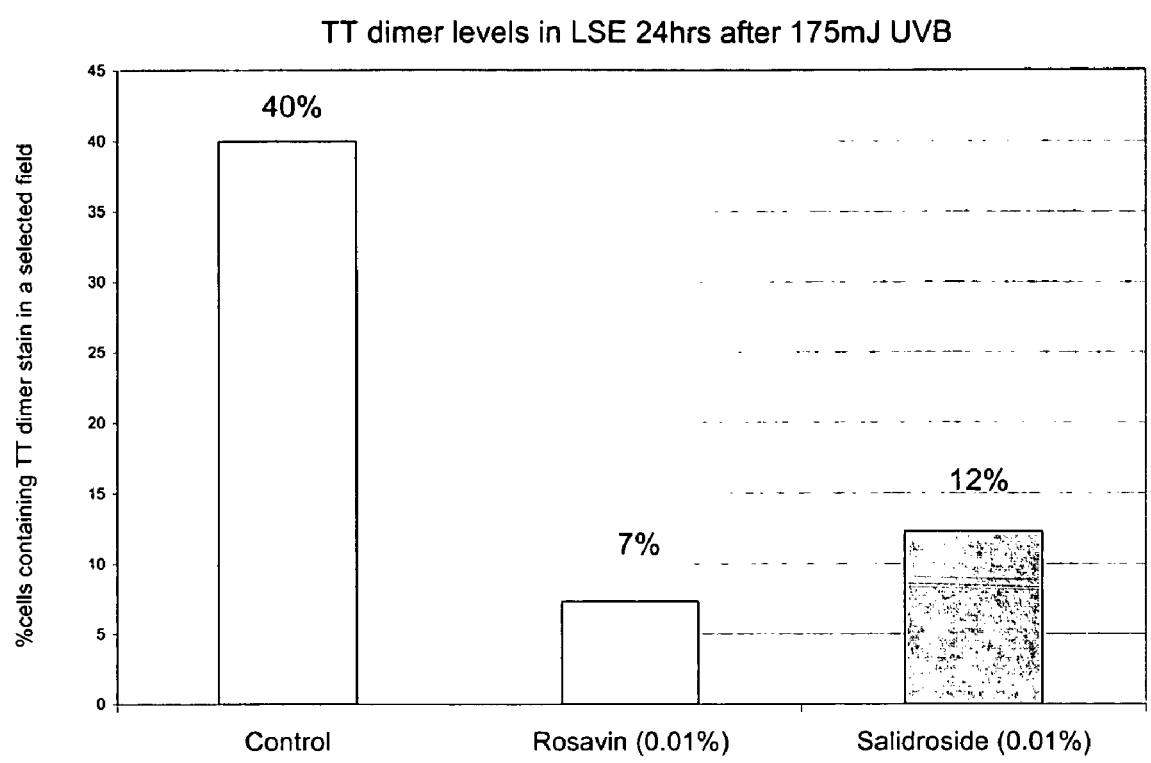
FIG. 2 provides a graphical depiction of the effect of actives of *Rhodiola rosea* on DNA repair/damage.

Results and Discussion: As seen in FIG. 1, UVB induces a dose-dependent increase of sunburn cell formation in living skin equivalents. There are 10, 21 and 32 sunburn cells in a selected field at 100 mJ, 150 mJ, and 200 mJ UVB radiation, respectively (FIG. 1 & 2 left side). In the LSEs pre-treated with *rhodiola rosea*, there are 2, 10, and 14 sunburn cells in a selected field at 100 mJ, 150 mJ, and 200 mJ UVB radiation, respectively. Pre-treatment with *Rhodiola rosea* significantly reduces the formation of sunburn cells via UVB irradiation. *Rhodiola rosea* pre-treatment is found to significantly reduce UVB induced sunburn cell formation in LSE.

EXAMPLE 2

Excised portions (8 mm) are taken from living skin equivalents (LSE) and cultured over transwell membrane plates. These excised portions are pre-treated with rosavin or salidroside at 0.01% (PBS) for 18 hours. After the post-incubation, these excised portions are UVB-irradiated at 0 and 175 mJ/cm$^2$. One set of LSEs is immediately fixed in formalin to determine TT dimer formation (DNA damage). Following a 24-hour post-incubation, another set of skin equivalents is fixed in formalin. These samples are then prepared for TT dimer immunostaining. Sections are then evaluated using a microscope at 400× magnification. A section is selected from each sample and TT dimer containing cells are evaluated. DNA damage is measured by examining TT dimer stained cells immediately after UVB irradiation. DNA repair (TT dimer removal) in UVB-irradiated LSEs is determined by comparing the levels of TT dimer at 0 hr (immediately after UVB) with the levels of TT dimer at 24 hours (24 hours after UVB).

Results & Discussion: As seen in FIG. 2, UVB induces an increase in DNA damage cells (TT dimer stained) in living skin equivalents with or without rosavin or salidroside pre-treatment. In the control, TT dimer levels in LSE are found to be at 40%, 24 hours after 175 mJ of UVB. In rosavin-treated LSE, TT dimer levels are at 7%, 24 hours after 175 mJ of UVB. In salidroside-treated LSE, TT dimer levels are at 12%, 24 hours after 175 mJ of UVB. Twenty-four hours later, there is a significant reduction in DNA damaged cells in the LSE. In conclusion, the results of the experiment demonstrate that rosavin may be the active component in *Rhodiola rosea* in providing the protective effects observed from *Rhodiola rosea*.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic composition comprising:
    an extract of *Rhodiola rosea* wherein the extract comprises an effective amount of at least one phenylpropanoid selected from the group consisting of rosavin, rosin, and rosarin;
    a silicone selected from the group consisting of dimethicone, phenyl trimethicone, cyclomethicone, and mixtures thereof;
    an ingredient selected from the group consisting of carbomer, xanthan gum, and acrylates/C10-C30 alkyl acrylate crosspolymer; and
    a cosmetically acceptable vehicle.

2. The cosmetic composition of claim 1 wherein the extract further comprises at least 0.1% salidrosides.

3. The cosmetic composition of claim 1 wherein the extract further comprises at least from 0.001% to 0.1% of tyrosol.

4. The cosmetic composition of claim 1 further comprising a sunscreen selected from the group consisting of water soluble sunscreens, oil soluble sunscreens, inorganic sunscreens, and organic sunscreens.

5. The cosmetic composition of claim 1 wherein the extract of *Rhodiola rosea* comprises from 1% to 50% rosavin and from 0.1% to 50% salidrosides.

* * * * *